United States Patent [19]

Ezzell et al.

[11] 4,358,412
[45] Nov. 9, 1982

[54] PREPARATION OF VINYL ETHERS

[75] Inventors: Bobby R. Ezzell, Lake Jackson; William P. Carl, Angleton; William A. Mod, Lake Jackson, all of Tex.

[73] Assignee: The Dow Chemical Company, Midland, Mich.

[21] Appl. No.: 158,427

[22] Filed: Jun. 11, 1980

[51] Int. Cl.$^3$ .................. C07F 9/113; C07C 69/73; C07C 143/70
[52] U.S. Cl. .................. 260/968; 260/950; 260/543 H; 560/183
[58] Field of Search .................. 260/968, 543 H; 560/183

[56] References Cited

U.S. PATENT DOCUMENTS

| | | | |
|---|---|---|---|
| 2,393,967 | 2/1946 | Brubaker | 260/30 |
| 2,559,752 | 7/1951 | Berry | 260/29.6 |
| 2,593,583 | 4/1952 | Lontz | 260/92.1 |
| 3,041,317 | 6/1962 | Gibbs et al. | 260/79.3 |
| 3,114,778 | 12/1963 | Fritz et al. | 260/614 |
| 3,180,895 | 4/1965 | Harris, Jr. et al. | 568/685 |
| 3,214,478 | 10/1965 | Milian, Jr. | 260/615 |
| 3,242,218 | 3/1966 | Miller | 260/915 |
| 3,250,806 | 5/1966 | Warnell | 260/535 |
| 3,282,875 | 11/1966 | Connolly et al. | 260/29.6 |
| 3,301,893 | 1/1967 | Patman et al. | 260/513 |
| 3,321,532 | 5/1967 | Lorenz | 568/685 |
| 3,450,684 | 6/1969 | Darby | 526/247 |
| 3,536,733 | 10/1970 | Carlson | 260/348.5 |
| 3,560,568 | 2/1971 | Resnick | 260/513 |
| 3,784,399 | 1/1974 | Grot | 117/62.1 |
| 3,909,378 | 9/1975 | Walmsley | 204/98 |
| 3,969,285 | 7/1976 | Grot | 260/2.2 R |
| 4,025,405 | 5/1977 | Dotson et al. | 204/98 |
| 4,035,254 | 7/1977 | Gritzner | 204/98 |
| 4,035,255 | 7/1977 | Gritzner | 204/98 |
| 4,065,366 | 12/1977 | Oda et al. | 204/98 |
| 4,085,071 | 4/1978 | Resnick et al. | 260/22 R |
| 4,126,588 | 11/1978 | Ukihashi et al. | 521/31 |
| 4,138,426 | 2/1979 | England | 260/465.6 |
| 4,151,053 | 4/1979 | Sekor et al. | 204/98 |
| 4,192,725 | 3/1980 | Dotson et al. | 204/98 |
| 4,197,179 | 4/1980 | Easell et al. | 204/255 |

FOREIGN PATENT DOCUMENTS

| | | |
|---|---|---|
| 54-118597 | 4/1979 | Japan . |
| 1406673 | 9/1975 | United Kingdom . |
| 1497748 | 1/1978 | United Kingdom . |
| 1497749 | 1/1978 | United Kingdom . |
| 1518387 | 7/1978 | United Kingdom . |

OTHER PUBLICATIONS

Derwent Abstract of German 1,238,458, vol. 7, No. 20, 4/1967.
Fern, et al., "J. of Polymer Science", Part A-1, vol. 4, (1966), pp. 131-140.
Chambers, "Fluorine in Organic Chem.", pp. 211-212, J. Wiley & Sons (1973).
Evans et al., "J. Organic Chem.", vol. 33, (1968) pp. 1837-1839.
Hudlicky, "Chem. of Org. Fluorine Cpds.", 2nd Ed., J. Wiley & Sons, N.Y., pp. 20-21.
Seko, "Comm. Operation of the Ion Exchange Membrane Chlor-Alkali Process", presented to ACS 4/4-9/1976.
Seko, "The Asahi Chem. Membrane Chlor-Alkali Process", The Chlorine Institute 2/9/1977.
Grot et al., "Perfluorinated Ion Exchange Membranes" presented to Electrochemical Soci. 5/7-11/1972.
Hora et al., "Nafion ® Membranes Structured for High Efficiency Chlor-Alkali Cells", presented to Electrochemical Soc. 10/1977.
Ukihashi et al., "Ion Exchange Membrane for Chlor-Alkali Process, presented to ACS 4/1977.
Olah, "Aldrichimica Acta", vol. 12, 1979, pp. 43-49.
Lovelace et al., "Aliphatic Fluorine Compounds", (1958), Reinhold NY., p. 107.
Munn, "Nafion ® Membranes", presented Electrochemical Soc. 10/1977.
Vaughn, "Nafion-an Electronic Traffic Controller".

Primary Examiner—Anton H. Sutto
Attorney, Agent, or Firm—James H. Dickerson, Jr.

[57] ABSTRACT

The invention relates to a process to produce compounds represented by the general formula

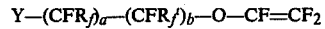

$$Y-(CFR_f)_a-(CFR'_f)_b-O-CF=CF_2$$

by decarboxylation of compounds represented by the general formula

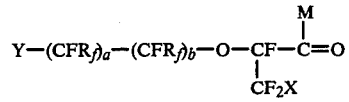

where a=0–3;
b=0–3;
provided a+b=2 or 3;
Y=an acid derivative;
X=Cl, I, or Br;
M=OR, F, Cl, Br, I, OA;
A=alkali metal, alkali earth metal, a quaternary nitrogen and hydrogen;
$R_f'$ and $R_f$ are independently selected from the group consisting of F, Cl, perfluoroalkyls and fluorochloroalkyls
R=an alkyl having one or more carbon atoms or an aryl.

11 Claims, No Drawings

PREPARATION OF VINYL ETHERS

BACKGROUND OF THE INVENTION

U.S. Pat. No. 3,450,684 teaches the following reaction:

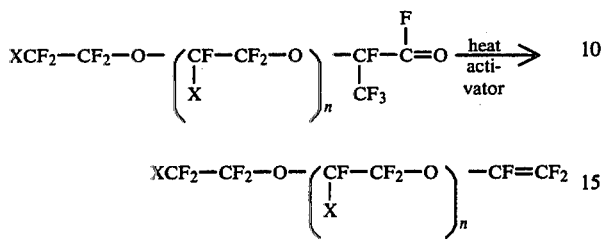

where X is F, Cl, H, CF$_2$H, CF$_2$Cl or CF$_3$ n is at least 1.

U.S. Pat. No. 3,560,568 teaches the following reaction:

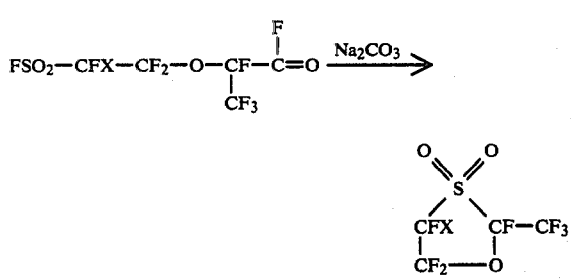

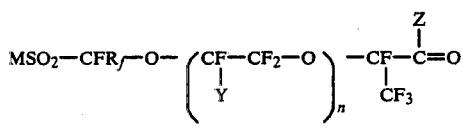

where X is F or CF$_3$

U.S. Pat. No. 3,282,875 teaches that compounds represented by the general formula

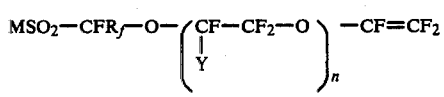

may be pyrolyzed at 200°–600° C. in the presence of a solid catalyst to compounds represented by the general formula MSO$_2$—CFR$_f$—O—(CF—CF$_2$—O)$_n$—CF=CF$_2$
                     |
                     Y where M is a radical selected from the group consisting of F, OH, amino, OMe Me is an alkali metal radical, or a quaternary ammonium radical Z is F or OX X is an alkali metal X is F or CF$_3$ n is 1 to 3

J. E. Fearn, et al teach in the Journal of Polymer Science, Vol. 4, Part A-1, p. 131–140, (1966) "Polymers and TerPolymers of Perfluoro-1,4,-pentadiene", that in the pyrolysis of the sodium salts of carboxylic acids which contain fluorine and chlorine in the beta position, sodium chloride is preferentially, but not exclusively eliminated. For example

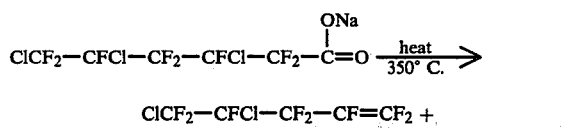

ClCF$_2$—CFCl—CF$_2$—CF=CF$_2$ +

ClCF$_2$—CFCl—CF$_2$—CCl=CF$_2$

U.S. Pat. No. 3,114,778 shows the pyrolysis of

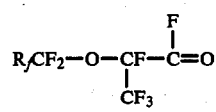

to a vinyl ether.

U.S. Pat. No. 4,138,426 shows the pyrolysis reaction

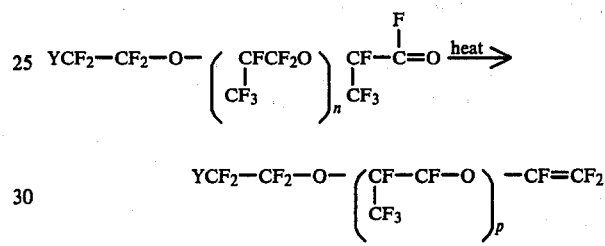

where

Y is —COOR, —COOH, —COOM or —CN

R is an alkyl group of from 1-6 carbon atoms

M is an alkali metal p is 1 to 5 n is 1 to 6

British Pat. No. 1,518,387 shows, and claims use of polymers from as membranes, compounds represented by the structure CF$_2$=CFOCF$_2$(CFXOCF$_2$)$_l$(CFX')$_m$(CF$_2$OCFX")$_n$—A where l is 0 to 3; m is 0 to 6; n is 0 to 4, and one of l and n is not 0; X,X' and X" are the same or different and respectively represent F or CF$_3$; A represents —C≡N, COF, COOH, COOR$_1$, COOM and CONR$_2$R$_3$ and R$_1$ represents C$_{1-10}$ alkyl group, R$_2$ and R$_3$ each represent a hydrogen atom or a C$_{1-10}$ alkyl group and M represents an alkali metal or a quaternary ammonium group.

Compounds, such as

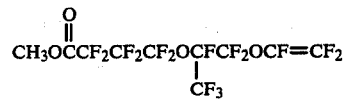

are shown as prepared by the addition of two equivalents of hexafluoropropylene oxide to one equivalent of

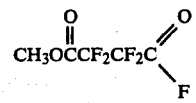

followed by decarboxylation to the vinyl ether. Compounds derived from the addition of one equivalent of the epoxide such as

are excluded by the general structure shown above.

R. D. Chambers, in his book, *Fluorine in Organic Chemistry*, published by John Wiley & Sons, 1973, pages 211–212, teaches that carboxylic acid derivatives may be converted to olefins. The conversion is taught to involve the loss of carbon dioxide and formation of an intermediate carbanion. The intermediate then looses NaF to form the resulting olefin.

BRIEF DESCRIPTION OF THE INVENTION

Compounds represented by the general formula

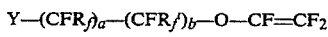

are prepared by decarboxylation of compounds represented by the general formula

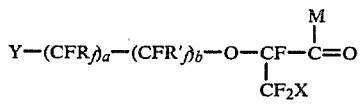

where
a=0–3
b=0–3
provided a+b=2 or 3
Y is an acid derivative
X=Cl, Br, or I
M=OR, F, Cl, Br, I or OA
A=alkali metal or quaternary nitrogen salt or hydrogen
$R_f$ and $R_f$ are independently selected from the group consisting of F, Cl, perfluoroalkyl and chlorofluoroalkyl
R is an alkyl group having one or more carbon atoms or aryl.

The decarboxylation is carried out at from about 50° C. to about 60° C. An activator such as a base, ZnO, silica or other known activators may be used.

DETAILED DESCRIPTION OF THE INVENTION

Based upon the known art, one would expect to produce cyclic compounds by decarboxylating compounds represented by the general formula

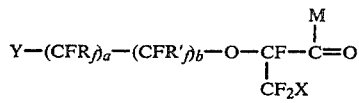

when Y is an acid derivative having a group displaceable by a nucleophile and when a+b=2 or 3.

This is the case as shown by U.S. Pat. No. 3,560,568 which shows ring formation when Y=FSO$_2$, $R_f$=$R_f$=F, X=F and a+b=2.

It is generally accepted (see Chambers) that decarboxylations of acids or derivatives to olefins involves loss of carbon dioxide to form an intermediate carbanion. When Y contains a leaving group which can be displaced by a nucleophile, and a+b=2 or 3 such that a 5 or 6 membered ring can be formed by displacing that leaving group from Y with the intermediate nucleophilic carbanion, then the 5 or 6 member ring would be the expected product. It is well known that because of the proximity of reactive groups involved in forming 5 or 6 membered rings and the stability of these rings, that formation of the rings is highly favored.

During the decarboxylation reaction of U.S. Pat. No. 3,560,568 the following sequence is expected to occur which forms a reactive carbanion intermediate according to the following and then cyclizes to a cyclic sulfone from that intermediate.

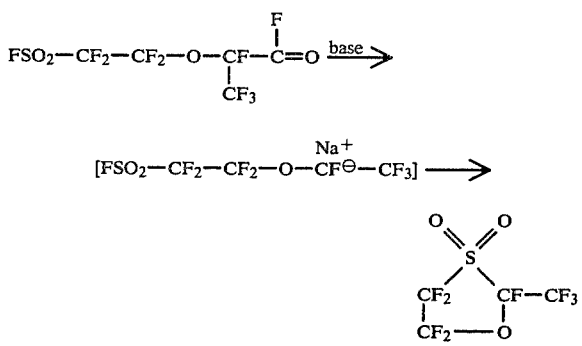

In this intermediate there is located a nucleophile (the carbanion) in a position such that formation of a 5 membered ring is possible by reaction of the carbanion with the sulfur, displacing F, to form NaF. This ring formation is shown by the patent and is confirmed by our comparative Example 1.

Ring formation is expected not only with FSO$_2$ but with other groups which fit the above description. For example, it is well known that carboxylic acid halides and phosphonic acid halides and esters readily react with nucleophiles such as OH$^-$, or carbanions, such as methyl lithium, displacing the halide or alkoxide from the carbonyl or phosphoryl.

However, it has been unexpectedly found that a linear olefin results when X is Cl, I, or Br, as opposed to the prior art where X was F.

The following compounds do not form rings during decarboxylation, although ring formation would be expected, but rather, they form linear, vinyl ether monomers useful in polymer synthesis, as shown by the following reaction:

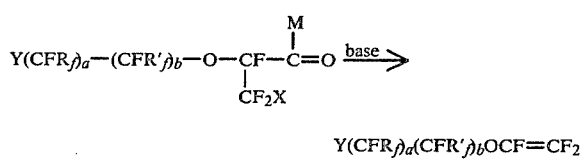

$Y(CFR_f)_a(CFR'_f)_bOCF=CF_2$ where
a=0–3
b=0–3
provided a+b=2 or 3,
Y is an acid derivative,
X=Cl, Br, I,
M=OR, F, Cl, Br, I or OA,
A=alkali metal, alkali earth metal, quaternary nitrogen, or hydrogen;

$R_f'$ and $R_f$ are independently selected from the group consisting of F, Cl, perfluoroalkyl and chlorofluoroalkyl, R is an alkyl group having one or more carbons or aryl.

Even though all ring-forming conditions are met, reaction site on Y for displacement and 5 or 6 membered ring formation, reaction occurs to produce the olefin substantially completely. Substantially complete formation of olefin, rather than cyclic compounds, by NaX elimination, particularly NaCl, is indeed surprising and unexpected.

The decarboxylation is conducted according to known methods, such as those taught by Chambers. For example, the decarboxylation temperatures may be from about 50° C. to about 600° C. The decarboxylation reaction may be conducted in the presence of an activator. The activator may be a base such as sodium carbonate or ZnO, silica or other known activators.

Optionally, a dispersant may be used to enhance the decarboxylation reactions. Suitable dispersants should be unreactive and may include such materials as tetraglyme, diglyme or glyme.

It is particularly convenient to use a slurry of $Na_2CO_3$ in the above dispersants for the decarboxylation reactions.

In general formula, Y is an acid derivative. For example, Y may be

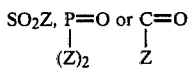

where Z is a leaving group such as OR, F, Cl, Br, or I and R is an alkyl radical having one or more carbon atoms or an aryl radical.

In the general formula, M may be OR, F, Cl, Br, I or OA where A is hydrogen, an alkali metal or a quaternary nitrogen and R is an alkyl radical having one or more carbon atoms or an aryl radical.

$R_f$ and $R_f'$ in the general formula, may be independently F, CL or a perfluoroalkyl or a chlorofluoroalkyl containing from one or more carbon atoms. a and b may independently represent an integer of 0 to 3, inclusive, provided that a+b is equal to 2 to 3.

In addition to unexpectedly forming vinyl ether compounds rather than cyclic compounds, it is also surprising that there is not evidence of formation of X substituted olefins. In the decarboxylation reaction either NaX can be eliminated to form $\sim OCF=CF_2$ of NaF can be eliminated to form $\sim OCF=CFX$. While it is not surprising that elimination of NaX predominates, it is surprising, particularly when X=Cl, to have substantially exclusive elimination of NaX. Fearn reports the preferential elimination of chloride from pyrolysis of sodium salts of carboxylic acids which contain both fluorine and chlorine in the β position, but not exclusive elimination of chloride. Fearn actually isolated some of the product resulting from fluoride elimination. No evidence, by I.R., Mass Spectrocopy or $F^{19}$ NMR, has shown indications of NaF elimination in the decarboxylation reactions of the present invention.

The discovery described herein represents a marked improvement over methods of the prior art for producing acid derivative functional vinyl ethers having three or four atoms, inclusive, between the functional group and the vinyl group. As discussed previously, formation of cyclic compounds resulted when decarboxylation reactions were used.

There is one reported method to prepare the compound $FSO_2CF_2CF_2OCF=CF_2$ (U.S. Pat. No. 3,560,568). In this patent is taught the following sequence:

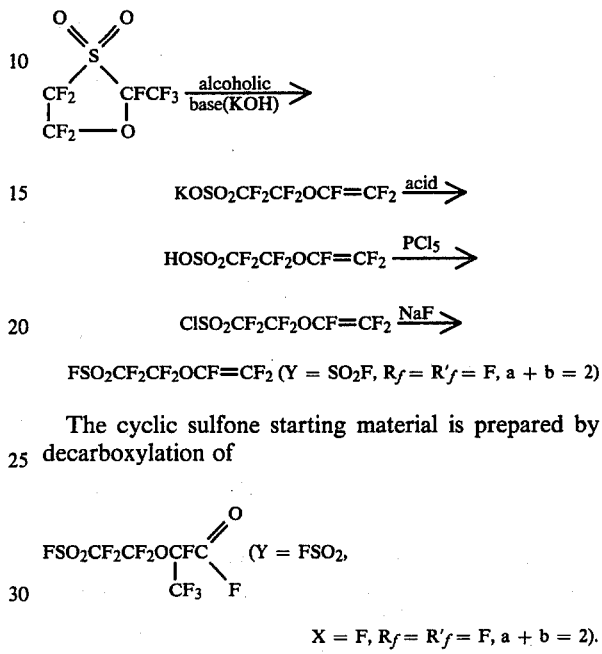

$FSO_2CF_2CF_2OCF=CF_2$ (Y = $SO_2F$, $R_f = R_f' = F$, a + b = 2)

The cyclic sulfone starting material is prepared by decarboxylation of $$FSO_2CF_2CF_2OCFC\underset{CF_3}{\overset{\displaystyle\nearrow O}{\underset{|}{\phantom{C}}}}\diagdown F \quad (Y = FSO_2,$$

X = F, $R_f = R_f' = F$, a + b = 2).

Clearly, all of the steps shown by the above sequence are in addition to the reaction of the present invention. The same reaction as used for making the starting cyclic sulfone for the above sequence is the only reaction required for making the desired vinyl ether monomer in the present invention.

It is important to have the sulfonyl fluoride group in the vinyl ether monomer rather than having the sulfur present as sulfonic acid or the acid salt. Polymers and copolymers with other vinyl monomers made from the sulfonyl fluoride form of the monomer, and hence having the sulfonyl fluoride in the resulting polymers, are thermoplastic and can thus be fabricated into films, pellets and the like by conventional plastic fabrication techniques such as melt extrusion. Once fabricated, the polymers can then be hydrolyzed, with base, to the sodium salt of the acid which can then be easily converted to the sulfonic acid with a variety of commercial acids such as HCl, $HNO_3$, $H_2SO_4$, and the like. Representative of these conversions are:

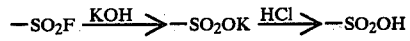

These materials, in the acid and salt forms, are extremely useful as solid acid catalyst and ion exchange membranes, particularly as membranes in electrolytic chlor-alkali cells.

Preparation of the polymers with the monomer in the acid or salt form results in polymers with the functional group in the same form and renders the polymers essentially unfabricatable by conventional fabrication techniques.

The above arguments apply equally well when Y=COZ and $PO(Z)_2$. The fact that it is desirable to have Z equal halogen, OR or the like so that thermoplastic polymers can be formed, fabricated and then easily converted to the acid or salt form means that Z must be a leaving group. Formation of the vinyl ether monomers by decarboxylation and having the properties provided by Z in the polymers as discussed above are mutually exclusive when X=F. The values provided for X in the present invention allow formation of the monomers by the one, simple, decarboxylation step and provide all of the desirable properties for the subsequently formed polymers.

EXAMPLES

EXAMPLE 1

300 ml of dry tetraglyme and 62.2 grams anhydrous $Na_2CO_3$ were added to a 1000 ml 3 neck flask equipped with a magnetic stirrer, thermometer, reflux condenser and an inlet port. Two $-78°$ C. cold traps were located in series downstream of the reflux condenser. 154 grams of product containing 92.1%

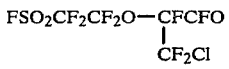

as identified by GCMS and VPC analyses were added dropwise. There was a slight temperature rise from 22° C. to about 35° C. over the period during the addition. Temperature of reactor was increased to 82° C. At this temperature there was obtained considerable reflux. The reflux condenser was removed and the product collected in the cold traps. The temperature was raised to 150° C. with the system under vacuum. 80.5 gms of the product was collected in first cold trap and 1 gm in the second. The product was analyzed by VPC and IR. Essentially all of the starting material had reacted. The yield to the n=o product ($FSO_2CF_2CF_2OCF=CF_2$) was 70.6% as a product analyzing 95% $FSO_2CF_2CF_2OCF=CF$ by VPC. IR analysis showed bands as follows:

| Vinyl Ether | 1830 wave no. (cm$^{-1}$) |
| --- | --- |
| —SO$_2$F | 1460 wave no. |
| —SO$_2$F | 1240 wave no. |
| —SF | 810 wave no. |
| VPC | |
| B. Pt. = 75°–76° C. | |

A direct titration of the unsaturation in the above product with $Br_2$ in $CCl_4$ was done to further confirm the structure. Twenty milliliters of $CCl_4$ solution containing 2 g $Br_2$ was made up as titrant. Two grams of the monomer was dissolved into 5 ml $CCl_4$ and titrated at ambient temperature to the point of color persistance. The titration required 10.9 ml of the bromine solution or 0.0068 moles of bromine. The apparent molecular weight of the monomer is then (2 g)/(0.0068) moles=293.6 or a difference from the proposed structure of $$\frac{293.6 - 280}{280} \times 100 = 5.4\%.$$

This value is in excellent agreement with the purity indicated by VPC analysis:

COMPARATIVE EXAMPLE 1.

100 ml of tetraglyme and 9.84 gms anhydrous $Na_2CO_3$ were added to a 500 ml 3 neck flask equipped with a magnetic stirrer, thermometer $-78°$ C. reflux condenser, and a dropping funnel. Two $-78°$ C. cold traps were located in series downstream of the reflux condenser. 29.35 grams of product analyzing 84.4%

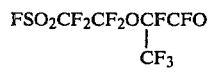

by VPC were added dropwise over a 3 hour period with evolution of $CO_2$. The reflux condenser was removed. The reactor was heated to 78° C.-80° C. while maintaining a slight $N_2$ sweep through the reactor to remove the product. 15.69 grams were recovered in the first cold trap and 0.6 grams in the second. The product was analyzed by VPC and IR. Conversion of the

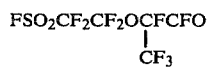

was essentially complete giving a yield of 77% to a product which was not a fluorosulfonylperfluoro vinyl ether. IR analysis showed bands as follows:

| Wave No. (cm$^{-1}$) | |
| --- | --- |
| 1360 | $\begin{matrix} O \\ -S- \\ O \end{matrix}$ |
| 1150 | $\begin{matrix} O \\ -S- \\ O \end{matrix}$ |
| B. Pt. ~80° C. | |

The product was believed to be the sulfone

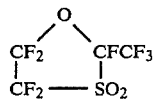

described in U.S. Pat. No. 3,560,568.

EXAMPLE 2

Using a procedure similar to Example 1,

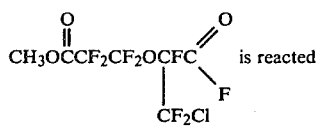

is reacted with a slurry of sodium carbonate in tetraglyme. After liberation of carbon dioxide,

is distilled from the reaction medium.

EXAMPLE 3

By the same procedure as Example 2,

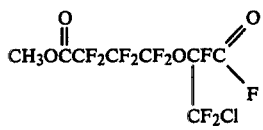

is decarboxylated to yield the vinyl ether

EXAMPLE 4

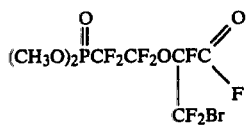

is reacted with a slurry of sodium carbonate in tetraglyme using conditions as described in Example 1. The linear vinyl ether,

is distilled from the reaction medium.

EXAMPLE 5

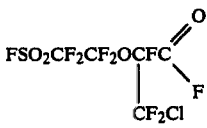

in methanol, is titrated with two equivalents of sodium hydroxide. Evaporation of the solvent gave, as a solid residue,

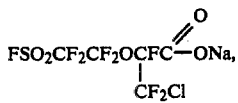

which was then pyrolyzed to give $FSO_2CF_2CF_2OCF=CF_2$.

We claim:

1. A method of preparing compounds represented by the general formula:
$Y(CFR_f)_a-(CFR'_f)_b-O-CF=CF_2$
which comprises decarboxylating

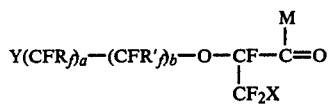

in the presence of an activator when M=OR, F, Cl, Br or I and at a temperature of from about 50° C. to about 600° C. for a time sufficient for said decarboxylation to occur where:

X = Cl, I or Br;

$R_f'$ and $R_f$ are independently selected from the group consisting of F, Cl, perfluoroalkyl radicals and fluorochloroalkyl radicals;

Z=OR, F, Cl, Br or I;

a=0-3;

b=0-3;

a+b=2 or 3;

M=OR, F, Cl, Br, I or OA;

A is selected from the group consisting of alkali metals, alkali earth metals, quaternary nitrogen and hydrogen; and R=an alkyl containing one or more carbon atoms or an aryl.

2. The method of claim 1 where Y is $SO_2Z$, Z=F, $R_f=R_f'=F$, and X=Cl.

3. The method of claim 1 where $$Y = C\begin{matrix}O\\ \diagup\\ \diagdown\\ OR\end{matrix},$$

$R_f=R_f'=F$ and X=Cl.

4. The method of claim 1 where $Y=PO(OR)_2$, $R_f=R_f'=F$.

5. The method of claim 1 where $Y=SO_2F$, $R_f=R_f'=F$, X=Cl and a+b=2.

6. The method of claim 1 wherein decarboxylation is carried out in the presence of an activator when M=OA.

7. The method of claim 1 where the activator is selected from the group consisting of sodium carbonate, ZnO and silica.

8. The method of claim 7 where the activator is sodium carbonate.

9. The method of claim 1 carried out in the presence of a dispersant.

10. The method of claim 9 where the dispersant is selected from the group consisting of tetraglyme, diglyme, glyme and a sodium carbonate slurry.

11. The method of claim 1 wherein the decarboxylation is carried out at a temperature of from about 50° C. to about 150° C.

* * * * *

UNITED STATES PATENT AND TRADEMARK OFFICE
CERTIFICATE OF CORRECTION

PATENT NO. : 4,358,412
DATED : Nov. 9, 1982
INVENTOR(S) : Bobby R. Exxell, William P. Carl, A. Mod It is certified that error appears in the above—identified patent and that said Letters Patent is hereby corrected as shown below:

Col. 1, line 62, delete "X" and insert --Y--.
Col. 3, line 45, delete "60°" and insert --600°--.
Col. 5, line 27, after "In" insert --the--;
        line 46, delete "2 to 3" and insert --2 or 3--;
        line 51, in the formula, delete "of" and insert --or--.
Col. 7, line 56, delete "persistance" and insert --persistence--.

Signed and Sealed this

Twenty-second Day of March 1983

[SEAL]

Attest:

GERALD J. MOSSINGHOFF

*Attesting Officer*  *Commissioner of Patents and Trademarks*